United States Patent

Kania

Patent Number: 5,164,467
Date of Patent: Nov. 17, 1992

[54] AZIRIDINE COMPOUNDS, ACRYLIC POLYMERS CONTAINING SAME AND COATING COMPOSITIONS CONTAINING SAID POLYMERS

[75] Inventor: Charles M. Kania, Natrona Heights, Pa.

[73] Assignee: PPG Industries, Inc., Pittsburgh, Pa.

[21] Appl. No.: 773,823

[22] Filed: Oct. 9, 1991

Related U.S. Application Data

[62] Division of Ser. No. 643,253, Jan. 22, 1991, Pat. No. 5,106,993.

[51] Int. Cl.$^5$ .......................... C08F 26/06
[52] U.S. Cl. .................... 526/258
[58] Field of Search ..................... 526/258

[56] References Cited

U.S. PATENT DOCUMENTS

| | | | |
|---|---|---|---|
| 3,480,601 | 11/1969 | Ashby et al. | 526/258 |
| 3,789,034 | 1/1974 | Wismer et al. | 528/48 |
| 4,563,307 | 1/1986 | Briden | 526/263 |
| 4,656,217 | 4/1987 | Sugiura et al. | 524/430 |

FOREIGN PATENT DOCUMENTS 847444  7/1970  Canada ................. 526/258

Primary Examiner—Joseph L. Schofer
Assistant Examiner—Alex H. Walker
Attorney, Agent, or Firm—Joseph J. Carducci; Linda Pingitore

[57] ABSTRACT

Aziridine compounds having the following structural formula:

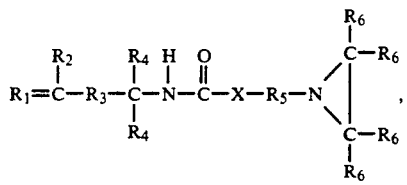

wherein
- $R_1$ represents an alkylidene group;
- $R_2$ represents hydrogen or an alkyl radical;
- $R_3$ represents an aromatic hydrocarbon moiety;
- $R_4$ represents an alkyl radical;
- $R_5$ represents an alkylene radical;
- $R_6$ represents hydrogen, an alkyl radical, phenyl or combinations thereof; and
- X represents oxygen, —S—, NH—, or NR—, wherein R represents an alkyl or phenyl are disclosed. Acrylic polymers containing moieties of at least two such aziridine compounds depending therefrom are also disclosed. The acrylic polymers are relatively non-toxic and have negligible inhalation irritation and are useful in the formulation of coating compositions which harden or cure at low temperatures.

5 Claims, No Drawings

AZIRIDINE COMPOUNDS, ACRYLIC POLYMERS CONTAINING SAME AND COATING COMPOSITIONS CONTAINING SAID POLYMERS

This is a divisional of application Ser. No. 07/643,253, filed Jan. 22, 1991, now U.S. Pat. No. 5,106,993 abandoned.

BACKGROUND OF THE INVENTION

Field of the Invention

The present invention relates to novel aziridine compounds and to novel acrylic polymers having aziridine-containing structural moieties as pendant groups. The invention more specifically relates to coating compositions containing said acrylic polymers suitable for use where hardening of the coating composition at low temperatures, for example, ambient temperature, is required.

BRIEF DESCRIPTION OF PRIOR ART

Known coating compositions which cure at low temperatures for use as automotive quality finishes, particularly as automotive refinishing compositions, include two-package compositions based on hydroxy-functional components and curing (crosslinking) agents containing isocyanate groups. However, the use of isocyanate-functional materials often requires that precautions be taken with respect to the handling and use of the isocyanates based on toxicity considerations. Such precautions can be relatively burdensome particularly when the coating compositions are utilized in environments not involving controlled factory conditions as exist, for example, in plants producing new automotive vehicles. For example, the application of automotive refinishing compositions tends to be done in refinishing shops under conditions which are not nearly as well controlled as those existing in automotive plants which manufacture original equipment. Accordingly, there is a need for high quality coating compositions which are not based on the utilization of isocyanate curing agents.

The present invention addresses these issues. The novel acrylic polymers bearing the pendant aziridine functional groups described and claimed in the present invention have been found to be useful in ambient temperature cured coatings. Surprisingly, the coatings have been found to be relatively non-toxic based on inhalation toxicology health data when compared to systems having known toxic behavior, for example, isocyanate-cured systems.

In U.S. Pat. No. 3,789,034 Wismer et al disclose the preparation of aziridine-functional polymers by preparing an aziridine-diisocyanate adduct and then reacting such adduct with hydroxy-bearing polymers. The aziridine-diisocyanate adduct is prepared, for example, by reacting a diisocyanate with 1,2-propylene imine in such a ratio so as to "half-block" the diisocyanate. Such a reaction does not lead solely to half-blocked products but also undesirable full-blocked products, which do not react with hydroxy-bearing polymers, and residual unreacted diisocyanate which will promote gelation when reacted with hydroxy-bearing polymers. Additionally, the products described by Wismer et al are urea-based, less reactive and do not possess the structure of any of the claimed subject matter herein.

Briden in U.S. Pat. No. 4,563,307 discloses the preparation of aziridine polymers, but not of the type claimed herein, involving the reaction of a specific isocyanate with an active hydrogen-containing aziridine.

In U.S. Pat. No. 4,656,217 Sugiura et al disclose a specific aziridine compound which is not consistent with the compounds claimed herein. Thus, the Sugiura et al compounds, $$(A)_m-(Q)_n-N\diagdown\diagup\begin{matrix}C-R_2\\|\\R_1\end{matrix}\begin{matrix}\\\\C-R_3\\|\\R_4\end{matrix}$$

are ureas, not urethanes.

SUMMARY OF THE INVENTION

The present invention is directed to an aziridine compound defined by the following structural formula:

$$R_1\!=\!C-R_3-\overset{R_4}{\underset{R_4}{C}}-\overset{H}{N}-\overset{O}{C}-X-R_5-N\diagdown\diagup\begin{matrix}C-R_6\\|\\R_6\end{matrix}\begin{matrix}\\\\C-R_6\\|\\R_6\end{matrix}\quad(I)$$

wherein
- $R_1$ represents an alkylidine group;
- $R_2$ represents hydrogen or an alkyl radical;
- $R_3$ represents an aromatic hydrocarbon moiety;
- $R_4$ represents an alkyl radical;
- $R_5$ represents an alkylene radical;
- $R_6$ represents hydrogen, an alkyl radical, phenyl or combinations thereof; and
- X represents oxygen, —S—, NH— or NR—, wherein R can be an alkyl having one to 12 carbon atoms, or even higher, or phenyl.

Each of the $R_4$ radicals can be similar to each other or different, and, similarly, each of the $R_6$ radicals can be similar to each other or different.

The present invention is also directed to an acrylic polymer having at least two aziridine-containing structural moieties as pendant groups described by the following structural formula:

$$I-A_n\!+\!R_1-\overset{R_2}{\underset{R_3}{C}}\!+\!-B_m-\!+\!R_1-\overset{R^2}{\underset{R_3}{C}}\!+\!D_p-T\quad(II)$$

with pendant groups:

$$\begin{matrix}R_4-C-R_4\\|\\N-H\\|\\C=O\\|\\X\\|\\R_5\\|\\N\\\diagup\diagdown\\R_6-C\text{———}C-R_6\\|\quad\quad\quad|\\R_6\quad\quad\quad R_6\end{matrix}$$

wherein R, $R_2$, $R_3$, $R_4$, $R_5$, $R_6$ and X are defined as above;

A, B and D, the same or different, are selected from the group consisting of the residues or moieties of
(1) ethylenically-unsaturated compounds, including those carrying substituents, provided such substituents are incapable of reacting with aziridine, and
(2) an aziridine compound defined by the following structural formula:

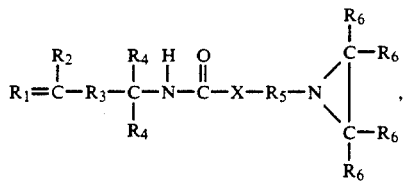

wherein $R_1$, $R_2$, $R_3$, $R_4$, $R_5$, $R_6$ and X are as defined above;

n, m and p are integers ranging, for example, from 0 to 100, or even higher; and I and T are defined, respectively, as initiator and terminator fragments well known to those skilled in free-radical polymerization reactions. An initiator can be a peroxide or an Azo compound. A terminator can be of the type thiol, haloalkane or 2,4-diphenyl-4-methyl-1-pentane.

The present invention is additionally directed to a curable coating composition containing said acrylic polymer bearing said aziridine containing structural moities, as defined above, and oligomers or polymers bearing moities capable of reacting with the said aziridine moities.

DETAILED DESCRIPTION OF THE INVENTION

The invention defined herein is directed to specific aziridine compounds and to acrylic polymers prepared therefrom.

The aziridine compounds claimed herein can be defined by the following structural formula:

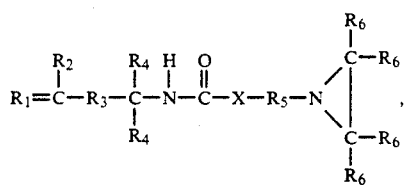

wherein $R_1$ represents an alkylidine group having one to three carbon atoms, preferably $CH_2=$;

$R_2$ represents hydrogen or an alkyl radical having one to three carbon atoms, preferably $CH_3-$;

$R_3$ represents a hydrocarbon moiety, e.g., a moiety such as phenylene, biphenylene or naphthalene, preferably phenylene;

$R_4$ represents an alkyl radical having from one to three carbon atoms, preferably $CH_3-$;

$R_5$ is an alkylene radical having one to three carbon atoms, preferably $-CH_2CH_2-$ or $-CH_2-CH_2-CH_2$;

$R_6$ represents hydrogen, an alkyl radical having one to three carbon atoms, phenyl or combinations thereof, preferably hydrogen; and X represents oxygen, $-S-$, $NH-$ or $NR-$, wherein R can be an alkyl having one to 12 carbon atoms, or higher, or phenyl, preferably oxygen.

The novel acrylic polymer having at least two pendant aziridine-containing structural moieties, also claimed herein, can be defined by the following structural formula:

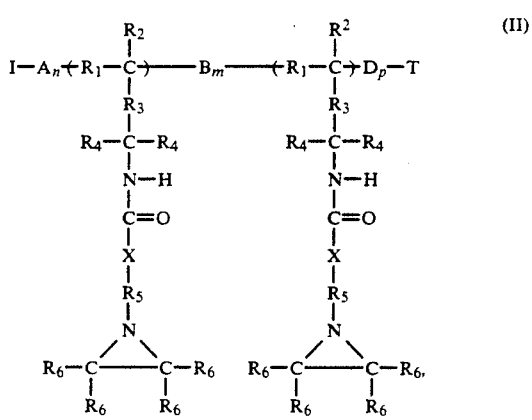

wherein $R_1$, $R_2$, $R_3$, $R_4$, $R_5$, $R_6$ and X are as defined above;

A, B and D, the same or different, are selected from the group consisting of the residues or moieties, of
(1) ethylenically-unsaturated compounds, including those carrying substituents, provided such substituents are incapable of reacting with aziridine; and
(2) an aziridine compound defined by the following structural formula:

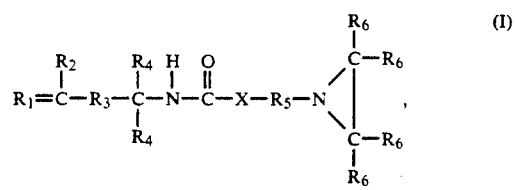

wherein $R_1$, $R_2$, $R_3$, $R_4$, $R_5$, $R_6$ and X are as defined above;

n, m, and p are integers ranging from 0 to 100, or even higher; and

I and T are defined as initiator and terminator fragments.

In the aziridine compound and in the acrylic polymer defined above, it is preferred that the radicals on the aromatic hydrocarbon moiety, defined by $R_3$, be located on the ring meta to each other. In the acrylic polymer defined above, I intend "pendant" to denote the groups attached to the polymer backbone.

The specific aziridine compound defined above, and claimed herein, can be prepared, for example, by reacting a monoisocyanate with an aziridine. The monoisocyanate used will have the following structural formula:

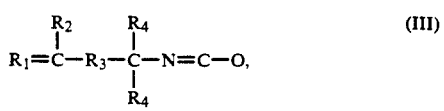

wherein $R_1$, $R_2$, $R_3$ and $R_4$ are as defined above. The aziridine compound reacted with the monoisocyanate will have the following structural formula:

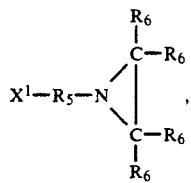 (IV)

wherein $R_5$ and $R_6$ are as defined above and X represents OH—, SH—, $NH_2$, HNR, wherein R can be an alkyl having one to 12 carbon atoms, or even higher, or phenyl or —N—$R_2$.

The reaction of the above monoisocyanate (III) with the above aziridine compound (IV) to obtain the novel aziridine monomer (I) can be carried out, for example, by bringing one equivalent of the monoisocyanate into contact with one equivalent of the aziridine compound at a temperature in the range of about 25° to about 45° C. for about one hour and then at a temperature of about 80° C. for an additional hour, and in the presence of a tin catalyst, such as an alkyl tin-containing catalyst.

The aziridine monomer so obtained (I) can then be polymerized (1) with itself to form a novel homopolymer falling within the definition of the acrylic polymer (II) or
(2) with one or more ethylenically-unsaturated compounds, including those carrying substituents, provided the substituents are incapable of reacting with aziridine, to form a heteropolymer also falling within the definition of the acrylic polymer (II).

Ethylenically-unsaturated compounds that can be used herein to form the desired copolymers include alkyl esters of acrylic acid or methacrylic acid, such as methyl methacrylate, ethyl methacrylate, butyl methacrylate, ethyl acrylate, butyl acrylate and 2-ethylhexyl acrylate. Suitable other copolymerizable ethylenically-unsaturated monomers include vinyl aromatic compounds, such as styrene and vinyl toluene; nitriles, such as acrylonitrile and methacrylonitrile; vinyl and vinylidene halides, such as vinyl chloride and vinylidene fluoride; and vinyl esters, such as vinyl acetate.

Additional ethylenically-unsaturated monomers that can be used to prepare the desired acrylic copolymers include hydroxyethyl acrylate, hydroxyethyl methacrylate, hydroxypropyl acrylate and hydroxypropyl methacrylate. Also the acrylic polymer can be prepared with N-(alkoxymethyl)acrylamides and N-(alkoxymethyl)methacrylamides.

The acrylic polymer can be prepared by solution polymerization techniques in the presence of suitable catalysts, such as organic peroxides or azo compounds, for example, benzoyl peroxide or N-N'-azobis-(isobutyronitrile). The polymerization can be carried out in an organic solution in which the monomers are soluble. Suitable solvents are aromatic solvents, such as xylene and toluene, and ketones, such as methyl amyl ketone. Alternatively, the acrylic polymer can be prepared by aqueous emulsion or dispersion polymerization techniques. Chain transfer agents can, optionally, be present.

However, as evident to those skilled in the art, the use of ethylenically-unsaturated monomers containing groups reactive with the isocyanate functionality is prohibited for the preparation of the isocyanate prepolymer.

Obviously, when an acrylic homopolymer is desired falling within the definition of (II) above, only the aziridine monomer (I) need be present. When an acrylic copolymer is desired falling within the definition of (II) above, the reaction mixture can contain from about 0.1 to about 75 weight percent, preferably from about five to about 50 weight percent, of the aziridine monomer (I), with the remainder being one or more of the ethylenically-unsaturated monomers, such as those defined above.

Another procedure than can be employed to prepare an acrylic polymer falling within the definition of (II) involves (a) homopolymerizing the ethylenically-unsaturated monoisocyanate falling within the definition of (III), or
(b) copolymerizing the ethylenically-unsaturated monoisocyanate falling within the definition of (III) with an ethylenically-unsaturated monomer, as described above, utilizing any conventional solution procedure which is well known in additional polymerization.

Procedures that can be used include those referred to above involving the polymerization of the novel aziridine compound (I). The isocyanate prepolymer so obtained is then reacted with the aziridine compound (IV) to obtain an acrylic homopolymer or heteropolymer falling within the scope of the acrylic polymer (II). This can be done, for example, by reacting the isocyanate-containing polymer or prepolymer on an equivalent basis with the aziridine compound (IV) under conditions wherein all, or substantially all, of the isocyanate in the isocyanate-containing polymer is consumed by the —OH, —SH, $NH_2$—, or NHR, wherein R can be an alkyl having one to 12 carbon atoms, or even higher, or phenyl, radicals on the aziridine compound.

The structure of the acrylic polymer (II) will depend largely on the procedure employed and on the components employed in its production. Thus, if the monoisocyanate (III) is homopolymerized and the resultant polymer is then reacted with the aziridine compound (IV), the pendant aziridine groups will always be identical to those shown therein and they will always be attached to each of the carbon atoms on the polymer backbone. If the novel aziridine compound defined by (I) is homopolymerized, the resulting acrylic polymer will be similarly structured. If, however, the mixture so polymerized contains the novel aziridine compound defined by (I) and at least one ethylenically-unsaturated monomer, as hereinabove described, then the resulting acrylic copolymer will reflect the composition of such reaction mixture and the moieties represented by A, B and D will be randomly distributed onto the polymer backbone in relationship to the defined pendant aziridine groups. Such random distribution, and also the polymer length, can also depend on the reaction conditions used and on the specific acrylic polymer desired.

The invention detailed herein can additionally be used for the preparation of curable coating compositions by combining with the novel acrylic polymer defined and claimed herein a component (oligomer or polymer) bearing structural moieties capable of reacting with the said structural aziridine moieties. Such reactive structural moieties can include carboxy, hydroxy, amine, epoxy, anhydride, amine/formaldehyde condensates and the like.

The results obtained herein are most surprising. The materials used above in the preparation of the novel acrylic polymers (II), that is, isocyanates and aziridines, are known to be highly toxic and yet the novel acrylic polymers, which are non-isocyanate but containing aziridines, have been found to be relatively non-toxic compared to isocyanate counterparts.

DESCRIPTION OF PREFERRED EMBODIMENTS

Example 1—Preparation of Aziridine Monomer

In a one-liter round-bottom flask, equipped with a stirrer, condenser, thermometer, nitrogen inlet and dropping funnel, there was charged 20 grams (1.0 mole) of m-TMI, an isocyanate obtainable from American Cyanamid ($\alpha,\alpha$-dimethyl isopropenyl benzyl isocyanate), and 144 grams of m-pyrol. The vessel was blanketed with nitrogen. At a temperature of 25° C., 87.0 grams of hydroxy ethylethyleneimine and 144 grams of m-pyrol were added to the vessel contents dropwise over a one-hour period while maintaining a temperature no greater than 45° C. Upon completion of the addition, 0.288 grams of dibutyl tin dilaurate was also added, and the mixture was heated to 80° C. and held at this temperature for 30 minutes or until the IR showed no NCO peak. Analysis by NMR confirmed that the aziridine monomer obtained had the following structural formula:

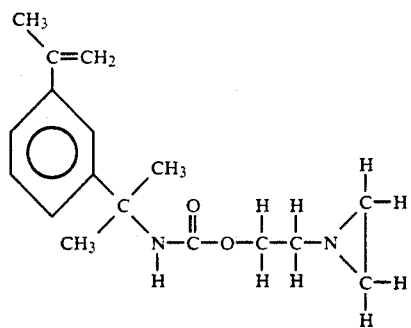

EXAMPLE 2—PREPARATION OF AZIRIDINE FUNCTIONAL ACRYLIC POLYMER

In a five-liter round bottom flask equipped with a paddle stirrer, thermometer, condenser and two dropping funnels, the initial charge, 192.0 grams of butyl acetate, was heated to reflux (124° C.), at which point two feeds, Feed A and Feed B were simultaneously added to the flask over a period of three hours while maintaining reflux conditions. Feed A contained 190.0 grams of butyl acrylate, 144.0 grams of styrene, 384.0 grams of methyl methacrylate and 480.0 grams of the aziridine monomer obtained in Example 1, and Feed B contained 192.0 grams of butyl acetate and 57.6 grams of VAZO-67 (2,2'-azobis-2-methyl-butyronitrile, available from duPont).

Upon completion of these feeds, there was added Feed C, and the reaction was maintained under the defined reflux conditions for one hour, after which Feed D was added, while maintaining the reflux conditions for an additional hour. Feed C contained 6.4 grams of butyl acetate and 4.8 grams of VAZO-67, while Feed D contained 9.6 grams of butyl acetate and 4.8 grams of VAZO-67. The product was analyzed and characterized as follows:

| | |
|---|---|
| Non-volatile content: | 57.1 weight percent |
| Viscosity: | 12.1 stokes |
| Color Value: | 3 |
| Peak Molecular Weight: | 10,700 |

(Determined by Gel Permeation Chromatography.)

EXAMPLE 3—PREPARATION OF AZIRIDINE FUNCTIONAL ACRYLIC POLYMER

In a five-liter round bottom flask equipped with a paddle stirrer, the thermometer, condenser and two dropping funnels, the initial charge, 1280.0 grams of xylene, was heated to reflux (140° C.), at which point Feed A was added to the flask over a period of 10 minutes and the reaction was returned to reflux (130° C.). Feed A contained 480.0 grams of butyl acrylate, 288.0 grams of styrene, 384 grams of methyl methacrylate and 192.0 grams of $\alpha,\alpha$-dimethyl isopropenyl benzyl isocyanate.

Feed B, 79.3 grams of t-butyl perbenzoate, was then added rapidly, with the reaction becoming exothermic, and the temperature rising to 134° C. The exotherm was allowed to subside (over a period of about 15 minutes) and then Feed C, containing 384.0 grams of methyl methacrylate and 192.0 grams of TMI, was added over a period of three hours, while maintaining reflux conditions (around 133°-135° C.). Upon completion of the addition of Feed C, the reaction was held at reflux for one hour.

Feed D, 165.3 grams of hydroxyethylethyleneimine, was then added rapidly to the reaction. An exotherm occurred and the reaction was held for 30 minutes at reflux (133° C.). Feed E, 1.92 grams of dibutyltin dilaurate, was then added, and the reaction was held at reflux one hour more or until the infrared showed no isocyanate band.

The product was analyzed and characterized as follows:

| | |
|---|---|
| Non-volatile content: | 57.3 weight percent in xylene |
| Viscosity: | 5.7 stokes |
| Color Value: | 1 |
| NCO Equivalents: | infinite |
| Peak Molecular Weight: | 10,139 |

(Determined by Gel Permeation Chromatography)

EXAMPLE 4—COATING COMPOSITION

A clear coating composition comprising the following materials was prepared by mixing the same.

| Component | Parts by Weight, Grams |
|---|---|
| Aziridine Acrylic from Example 3 | 115.2 |
| Polysiloxane solution[1] | 1.0 |
| U.V. Absorber[2] | 3.0 |
| Light Stabilizer[3] | 1.0 |
| Additive[4] | 0.6 |
| Toluene | 19.0 |
| Isobutyl Acetate | 38.4 |
| n-Amyl Propionate | 6.4 |
| Methyl-Amyl Ketone | 6.0 |
| Ethyl-3-Ethoxy Propionate | 16.8 |
| Oxo-Heptyl Ether Acetate | 42.3 |

| Component | Parts by Weight, Grams |
|---|---|
| Anhydride Resin[5] | 53.3 |

[1] Dow Corning DC-200, 135 csk. dissolved in xylene to give 0.5 percent polysiloxane solution
[2] Tinuvin 323 available from Ciba-Geigy Corporation
[3] Tinuvin 292 available from Ciba-Geigy Corporation
[4] BYK-300 available from BYK-MALLINCKRODT
[5] Maleic Anhydride functional acrylic polymer The clear coating composition described above was spray applied to 24 gauge cold rolled steel panels (treated with Bonderite 40, primed with DP-40/401, a two-component epoxy primer from PPG Industries, Inc., and base coated with Deltron ® Universal Basecoat from PPG Industries, Inc., PPG Finishes.

The clearcoat film was allowed to cure at ambient conditions to give a coating that had a 20 degree gloss of 90, D.O.I. of 40, Sward hardness of 16 and good resistance to solvents, gasoline and humidity.

In addition, an airborne sensory irritation study in mice with the above coating system was conducted in compliance with EPA Laboratory Practice Regulations (40 CFR Park 792).

Based on the $RD_{50}$ of 131 mg/m$^3$, negligible to very slight upper airway irritation in humans would be predicted at 1.3 to 13.1 mg/m$^3$ (L. E. Kane, C. S. Barrow, Y. Alarie, "A Short-Term Test to Predict Acceptable Levels of Exposure To Airborne Sensory Irritants," *American Industrial Hygiene Association Journal*, (40) 3/79, pp. 207-229.

According to the provisions of the patent statutes, there are described above the invention and what are now considered to be its best embodiments. However, within the scope of the appended claims, it is to be understood that the invention may be practiced otherwise than as specifically described.

What is claimed is:

1. An acrylic polymer having at least two aziridine-containing structural moieties as pendant groups defined by the following structural formula:

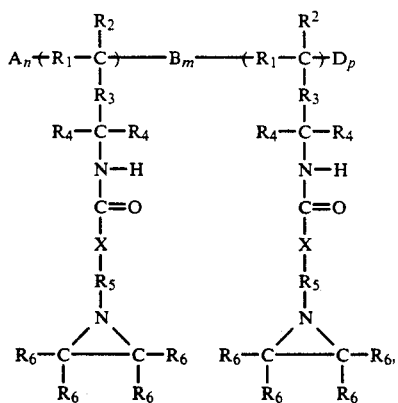

wherein
   R$_1$ represents an alkylidine radical;
   R$_2$ represents hydrogen or an alkyl radical;
   R$_3$ represents an aromatic hydrocarbon moiety;
   R$_4$ represents an alkyl radical;
   R$_5$ represents an alkylene radical;
   R$_6$ represents hydrogen, an alkyl radical, phenyl or combinations thereof;
   X represents oxygen, —S—, NH— or NR—;

A, B and D are selected from the group consisting of the moieties of
   (1) ethylenically-unsaturated compounds that will not react with aziridine and
   (2) an aziridine compound defined by the following structural formula:

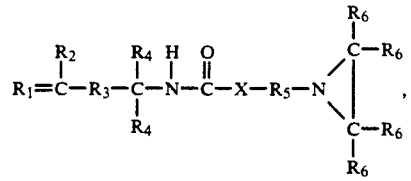

wherein R$_1$, R$_2$, R$_3$, R$_4$, R$_5$, R$_6$ and X are as defined above; and n, m and p are integers ranging from 0 to about 100 and higher.

2. The acrylic polymer of claim 1 wherein
   R$_1$ represents CH$_2$=;
   R$_2$ represents hydrogen or an alkyl radical having one to three carbon atoms;
   R$_3$ represents phenylene, biphenylene or naphthalene;
   R$_4$ represents an alkyl radical having one to three carbon atoms;
   R$_5$ represents an alkyl radical having one to three carbon atoms; and
   R$_6$ represents hydrogen, an alkyl radical having one to three carbon atoms or phenyl.

3. The acrylic polymer of claim 1 wherein R$_1$ represents CH$_2$=, R$_2$ represents CH$_3$—, R$_3$ represents a phenylene radical, R$_4$ represents CH$_3$—, R$_5$ represents —CH$_2$—CH$_2$—, R$_6$ represents hydrogen and X represents oxygen.

4. The acrylic polymer of claim 1 wherein R$_1$ represents CH$_2$=, R$_2$ represents CH$_3$—, R$_3$ represents a phenylene radical, R$_4$ represents CH$_3$—, R$_5$ represents —CH$_2$—CH$_2$—CH$_2$—, R$_6$ represents hydrogen and X represents oxygen.

5. A curable coating composition comprising (a) an acrylic polymer having at least two aziridine-containing structural moieties as pendant groups defined by the following structural formula:

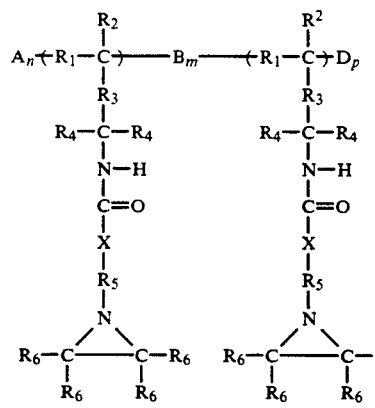

wherein
   R$_1$ represents an alkylidine radical;
   R$_2$ represents hydrogen or an alkyl radical;
   R$_3$ represents an aromatic hydrocarbon moiety;
   R$_4$ represents an alkyl radical;
   R$_5$ represents an alkylene radical;

$R_6$ represents hydrogen, an alkyl radical, phenyl or combinations thereof;

X represents oxygen, —S—, NH— or NR—, wherein R represents an alkyl or phenyl;

A, B and D are selected from the group consisting of the moieties of (1) ethylenically-unsaturated compounds that will not react with aziridine and (2) an aziridine compound defined by the following structural formula:

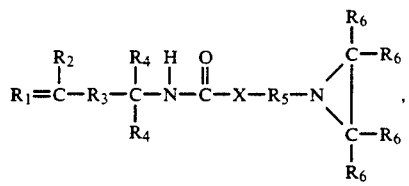

wherein $R_1$, $R_2$, $R_3$, $R_4$, $R_5$, $R_6$ and X are as defined above; and n, m and p are integers ranging from 0 to about 100 and higher, and (b) an oligomer or polymer bearing structural moities capable of reacting with the said structural aziridine moities.

* * * * *